United States Patent
Oguchi

(10) Patent No.: US 8,487,988 B2
(45) Date of Patent: *Jul. 16, 2013

(54) FINGERPRINT AUTHENTICATION APPARATUS AND FINGERPRINT AUTHENTICATION METHOD

(75) Inventor: Shinobu Oguchi, Tokyo (JP)

(73) Assignee: Empire Technology Development LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/362,062

(22) Filed: Jan. 31, 2012

(65) Prior Publication Data

US 2012/0127296 A1 May 24, 2012

Related U.S. Application Data

(63) Continuation of application No. 12/968,952, filed on Dec. 15, 2010, now Pat. No. 8,125,517.

(30) Foreign Application Priority Data

Apr. 28, 2010 (JP) ................................ 2010-103610

(51) Int. Cl.
*H04N 7/18* (2006.01)
*G06K 9/00* (2006.01)

(52) U.S. Cl.
USPC ........................................... 348/77; 382/124

(58) Field of Classification Search
USPC 382/124, 115, 127, 126, 116; 396/15; 348/77
See application file for complete search history.

(56) References Cited

U.S. PATENT DOCUMENTS

| 6,943,665 | B2 | 9/2005 | Chornenky |
| 8,125,517 | B2 * | 2/2012 | Oguchi ........................... 348/77 |
| 2003/0028784 | A1 | 2/2003 | Uchida |
| 2010/0208953 | A1 | 8/2010 | Gardner et al. |

FOREIGN PATENT DOCUMENTS

| JP | 04-092990 | 3/1992 |
| JP | 06-096195 | 4/1994 |
| JP | 11-250226 | 9/1999 |
| JP | 2002-298131 | 10/2002 |
| JP | 2004-118696 | 4/2004 |
| JP | 2004-363538 | 12/2004 |
| JP | 2005-514687 | 5/2005 |
| JP | 2007-202879 | 8/2007 |

OTHER PUBLICATIONS

Hiroyuki Baba, et al "Effects of batericidal against *Staphylococcus aureus* particles of titanium dioxide photocatalyst solution" Experts Papers from the 23rd Annual Meeting, Feb. 13, 2009 [Online: http://nanowave.org/blog/archives/2009/02/post_12.html].
Biometrics, Wikipedia [Online: http://en.wikipedia.org/wiki/Biometrics] retrieved on Nov. 22, 2010.

(Continued)

*Primary Examiner* — Behrooz Senfi
(74) *Attorney, Agent, or Firm* — Maschoff Brennan

(57) ABSTRACT

A fingerprint authentication apparatus and a fingerprint authentication method are provided. The fingerprint authentication apparatus is configured to prevent infection from viruses or bacteria and quickly and accurately perform fingerprint authentication. The fingerprint authentication apparatus includes an irradiation section that irradiates a mounting section when a finger is not detected to prevent infection.

19 Claims, 6 Drawing Sheets

OTHER PUBLICATIONS

Horiuti Kahori Wet fingers, finger dry—in fact Fingerprint (Introduction, Part One and Part Two) Mar. 29, 2007 [Online: http://itpranikkeibp.cojp/article/COLUMN/20070227/263427/?ST=security&P=2].

"Solid Optical Fingerprint Sensor: SEF-AI FI" [Online: http://www.mitsumi.cojp/Catalog/pdf/finger_sef al fl .pdf] retrieved on Dec. 15, 2010.

"Exploring the "now" (Biometrics) Authentication Biometrics," Safety Japan, BP Net, Nikkei Business Publications, Inc, accessed at (http://www.nikkeibp.co.jp/sj/2/special/43/index4.html), accessed on Dec. 14, 2012, pp. 3.

"Grant Implementation Technique Producing a Micro-Cooling System with a Cooling Capacity of More Than 100w/Cm 2 in a Space-Saving," vol. 35 , Sep. 16, 2008, accessed at http://web.archive.org/web/20100323154649/http://www.nedo.go.jp/informations/press/200916_1/200916_1.html, pp. 5.

* cited by examiner

FINGERPRINT AUTHENTICATION APPARATUS AND FINGERPRINT AUTHENTICATION METHOD

CROSS-REFERENCE TO RELATED APPLICATIONS

This patent application is a continuation of U.S. patent application Ser. No. 12/968,952, filed Dec. 15, 2010, which claims priority to Japanese Patent Application No. 2010-103610, filed Apr. 28, 2010. The foregoing applications are incorporated herein by reference.

TECHNICAL FIELD

Embodiments disclosed herein relate to a biometric authentication apparatus and a fingerprint authentication method for performing personal authentication using a fingerprint of a user.

BACKGROUND

A password, a signature, a stamp seal, and the like have conventionally been used to perform personal authentication. However, personal authentication using them suffers from problems. More specifically, forgetting a password or losing a stamp may prevent the user from authenticating himself/herself. Leakage of the password or theft of the stamp may lead to the authentication of others. For this reason, a biometric authentication (biometrics authentication) technique for performing personal authentication using information such as a physical trait or behavioral trait of a user has recently been adopted. Biometric authentication is capable of preventing a third party other than the user from being authenticated. Biometric authentication cannot be forgotten or lost.

At present, fingerprint authentication using a user's fingerprint is widely prevalent as one of the readily available, reliable biometric authentication techniques. A general fingerprint authentication apparatus used for fingerprint authentication is provided with a sensor for reading a fingerprint (e.g., an optical sensor, a capacitive sensor, a field intensity measuring sensor, or a pressure-sensitive sensor). The fingerprint authentication apparatus confirms the identity of a user by forming an image of information read by means of the sensor and performing comparisons.

It is known that if a finger used at the time of fingerprint authentication has adequate moisture, a success rate of fingerprint identification improves to allow quick and accurate fingerprint authentication. A skin cream has been provided exclusively for fingerprint authentication. The skin cream provides adequate moisture to a finger and improves a success rate of fingerprint identification when the skin cream is applied to the finger in small amounts.

A solid optical fingerprint sensor capable of confirming the identity of a user by the interdigital scattered light method, even if the user uses his/her wet finger, has been introduced.

A conventional fingerprint authentication apparatus as described above is generally configured to perform authentication by reading a fingerprint of a finger mounted on a mounting section made of tempered glass or the like by means of a sensor. For example, if the fingerprint authentication apparatus is installed in an ATM at a financial institution or at the entrance of an apartment house, fingers of an indefinite number of users touch the mounting section. The fingerprint authentication apparatus may serve as a medium for the transmission of viruses or bacteria among users. The possibility of infection is expected to increase further when adequate moisture is provided to a finger for improving a success rate of fingerprint identification.

There is a need for a fingerprint authentication apparatus and a fingerprint authentication method capable of preventing infection from viruses or bacteria and quickly and accurately performing fingerprint authentication.

BRIEF SUMMARY

A fingerprint authentication apparatus according to some embodiments of the present disclosure includes a mounting section where a finger is to be mounted, an authentication section configured to authenticate a fingerprint of the finger mounted on the mounting section, a cover section forming a space where the finger can be inserted between the cover section and the mounting section and surrounding the mounting section, a finger sensor disposed at the cover section and configured to detect whether the finger is mounted on the mounting section, an ultraviolet irradiation section disposed at the cover section and configured to apply ultraviolet light toward the mounting section, an ultraviolet irradiation control section configured to control the ultraviolet irradiation section to apply the ultraviolet light when the finger sensor does not detect the finger being mounted, a temperature and humidity sensor configured to detect temperature and humidity of the space formed between the mounting section and the cover section, a dew-point temperature calculation section configured to calculate dew-point temperature from the temperature and the humidity measured by the temperature and humidity sensor, a mounting section cooling section configured to cool the mounting section to the dew-point temperature calculated by the dew-point temperature calculation section and cause condensation on a surface of the mounting section to be touched by the finger, and a photocatalyst-containing layer formed on at least the surface of the mounting section to be touched by the finger and containing a photocatalyst.

A fingerprint authentication apparatus according to some embodiments of the present disclosure includes a mounting section where a finger is to be mounted, an authentication section configured to authenticate a fingerprint of the finger mounted on the mounting section, a finger sensor configured to detect whether the finger is mounted on the mounting section, an ultraviolet irradiation section configured to apply ultraviolet light toward the mounting section, and an ultraviolet irradiation control section configured to control the ultraviolet irradiation section to apply the ultraviolet light when the finger sensor does not detect the finger being mounted.

The fingerprint authentication apparatus according to some embodiments of the present disclosure can further include a cover section forming a space where the finger can be inserted between the cover section and the mounting section and surrounding the mounting section. The finger sensor and the ultraviolet irradiation section can be disposed at the cover section.

In the fingerprint authentication apparatus according to some embodiments of the present disclosure, a photocatalyst-containing layer containing a photocatalyst can be formed on at least a surface of the mounting section to be touched by the finger.

The fingerprint authentication apparatus according to some embodiments of the present disclosure can further include a temperature and humidity sensor configured to detect temperature and humidity of the space formed between the mounting section and the cover section, a dew-point temperature calculation section configured to calculate dew-point temperature from the temperature and the humidity measured by the temperature and humidity sensor, and a mounting section cooling section configured to cool the mounting section to the dew-point temperature calculated by the dew-point temperature calculation section and cause condensation on a surface of the mounting section to be touched by the finger.

The mounting section cooling section can be configured to cause condensation on the surface of the mounting section to be touched by the finger when the finger sensor detects the finger being mounted.

The temperature and humidity sensor can be disposed at the cover section.

The fingerprint authentication apparatus according to some embodiments of the present disclosure can further include a hygroscopic substance absorbing moisture caused by the condensation in a region different from the surface of the mounting section to be touched by the finger.

A fingerprint authentication method according to some embodiments of the present disclosure is a fingerprint authentication method for authenticating a fingerprint of a finger mounted on a mounting section and can include detecting whether the finger is mounted on the mounting section, applying ultraviolet light toward the mounting section when the finger is not mounted on the mounting section, and authenticating a fingerprint of the finger when the finger is mounted on the mounting section.

In the fingerprint authentication method according to some embodiments of the present disclosure, a photocatalyst-containing layer containing a photocatalyst is formed on at least a surface of the mounting section to be touched by the finger. The method can further include causing ultraviolet light and the photocatalyst to react with each other to generate active oxygen when the ultraviolet light is applied toward the mounting section.

The fingerprint authentication method according to some embodiments of the present disclosure further includes moistening the finger mounted on the mounting section when the finger is mounted on the mounting section and is capable of authenticating the fingerprint of the moistened finger.

DETAILED DESCRIPTION

A fingerprint authentication apparatus according to an embodiment of the present disclosure will be described with reference to the drawings. Note that the embodiment to be described below is illustrative of the present disclosure and is not intended to limit the present disclosure to the embodiment. Thus, the present disclosure can be implemented in various forms without departing from the scope of the present disclosure.

Figure 1:
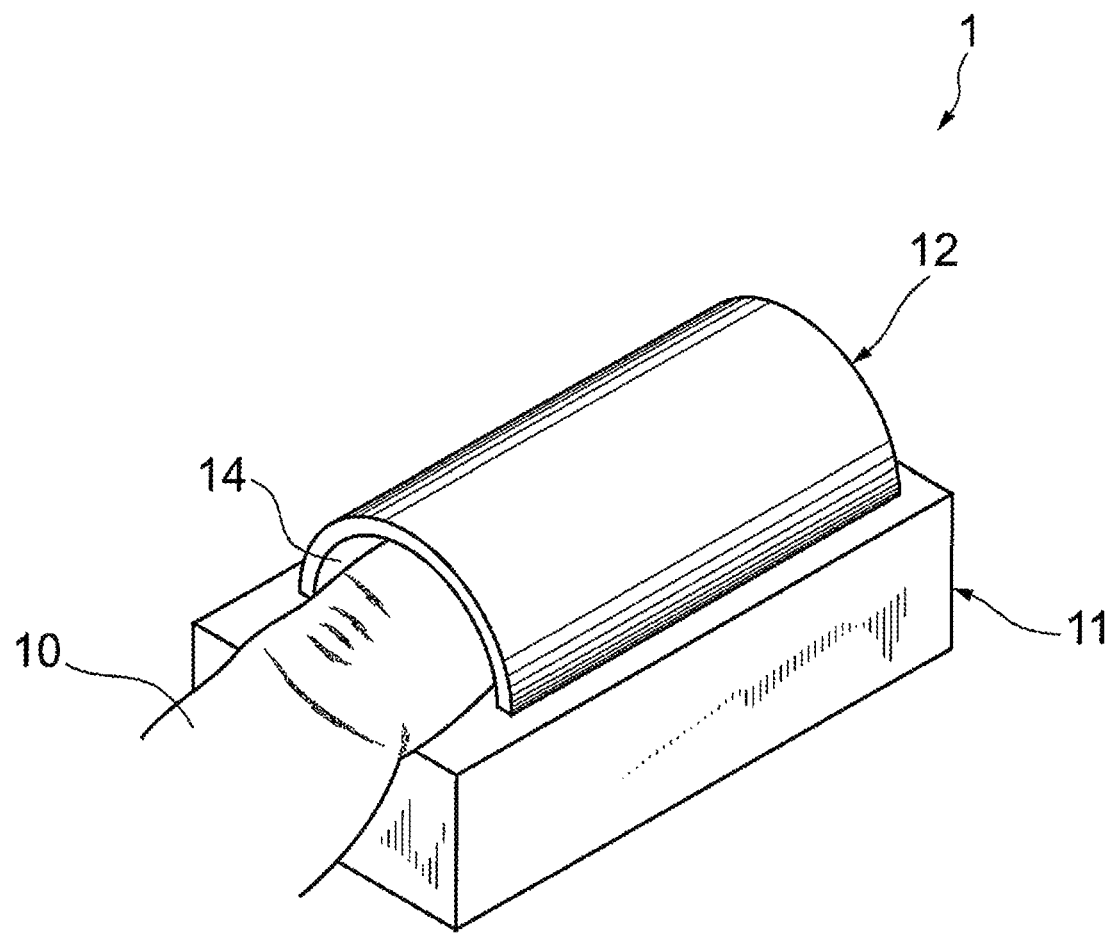
FIG. 1 is a perspective view of a fingerprint authentication apparatus according to an embodiment of the present disclosure.
Figure 2:
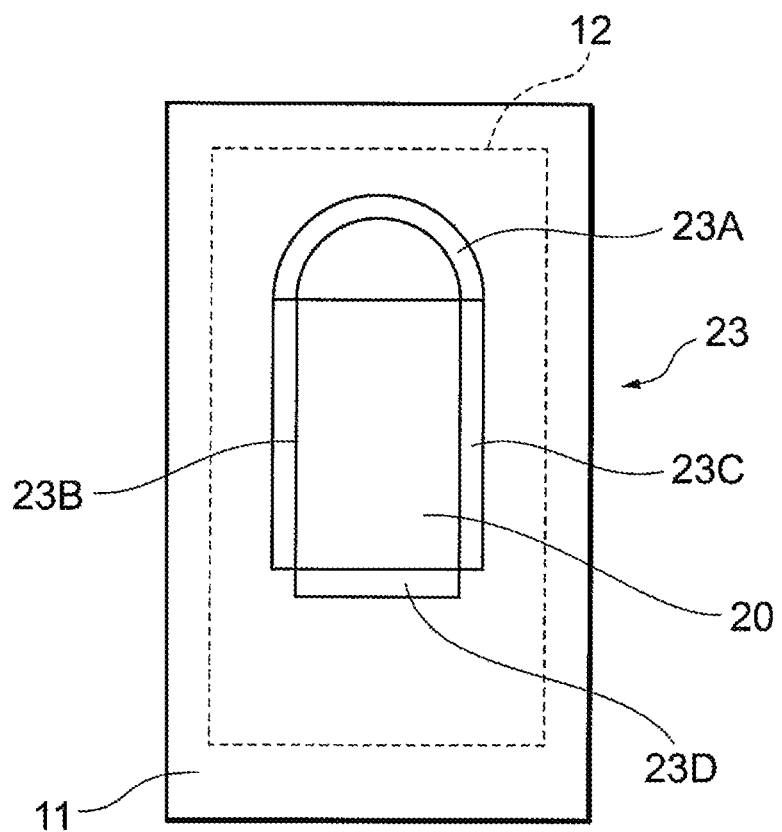
FIG. 2 is a plan view showing a state in which a cover section is removed from the fingerprint authentication apparatus shown in FIG. 1.
Figure 3:
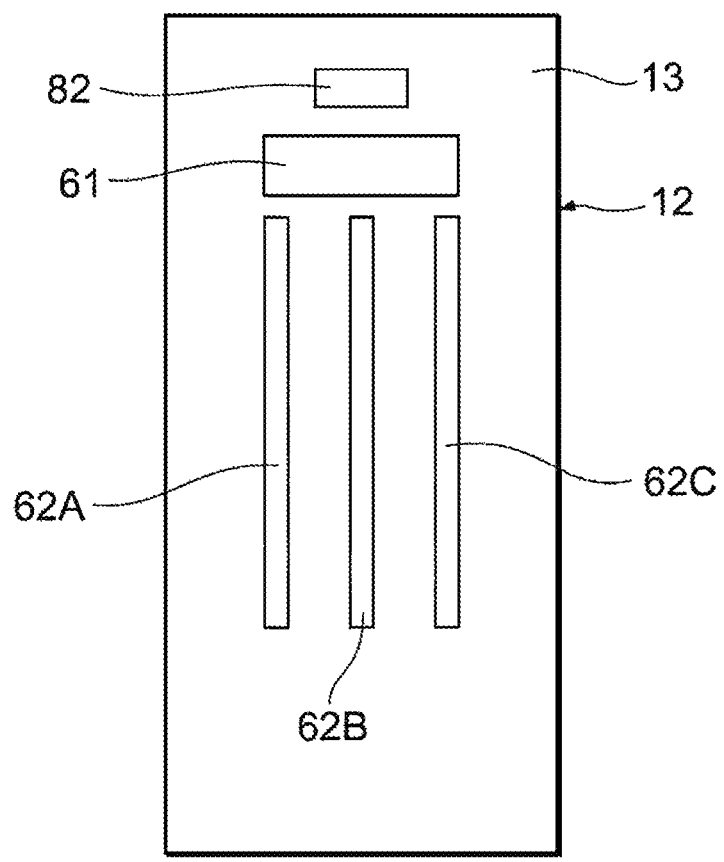
FIG. 3 is a plan view of an inner surface of the cover section of the fingerprint authentication apparatus shown in FIG. 1.
Figure 4:
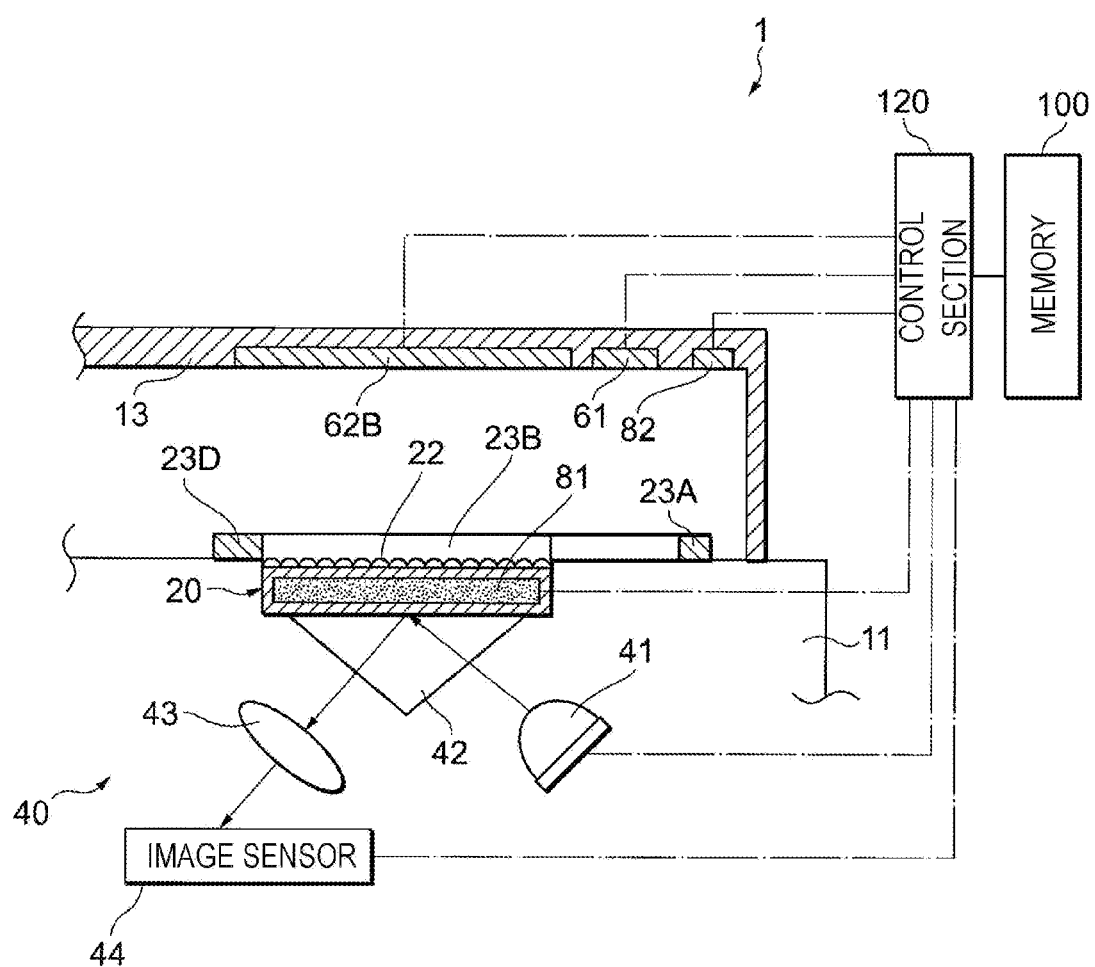
FIG. 4 is a configuration diagram showing, in cross section, a part of the fingerprint authentication apparatus shown in FIG. 1.
Figure 5:
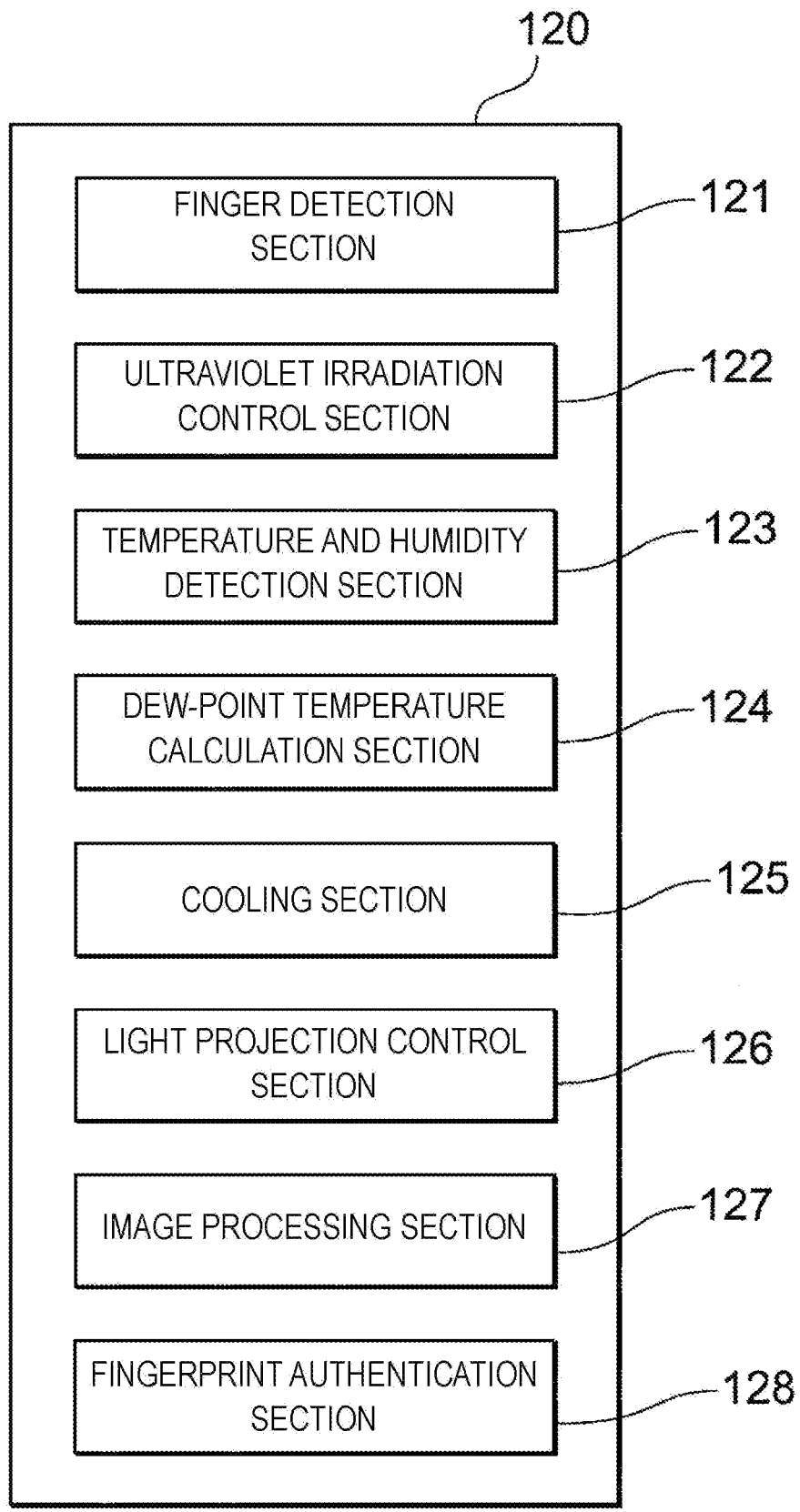
FIG. 5 is a block diagram showing an illustrative example of a functional configuration of a control section of the fingerprint authentication apparatus shown in FIG. 1.

FIG. 1 is a perspective view of the fingerprint authentication apparatus according to the embodiment of the present disclosure. FIG. 2 is a plan view showing a state in which a cover section is removed from the fingerprint authentication apparatus shown in FIG. 1. FIG. 3 is a plan view of an inner surface of the cover section of the fingerprint authentication apparatus shown in FIG. 1. FIG. 4 is a configuration diagram showing, in cross section, a part of the fingerprint authentication apparatus shown in FIG. 1. FIG. 5 is a block diagram showing an illustrative example of a functional configuration of a control section of the fingerprint authentication apparatus shown in FIG. 1. For ease of illustration, the ratios between the sizes including the thicknesses of members which are shown on an enlarged scale or on a reduced scale are made different from the actual ratios.

As shown in FIGS. 1 to 5, a fingerprint authentication apparatus 1 according to an embodiment of the disclosure includes a housing 11, a mounting section 20 which is disposed on an upper surface of the housing 11 and on which a finger 10 of a user is to be mounted, a dome-shaped cover section 12 which is disposed on the upper surface of the housing 11 and delimits a space between itself and the mounting section 20 into which the finger 10 of the user can be inserted, a finger sensor 61 which detects whether a finger is mounted on the mounting section 20, three ultraviolet irradiation lamps 62A, 62B, and 62C which apply ultraviolet light toward the mounting section 20, a micro cooling unit 81 which cools the mounting section 20 to dew-point temperature, a temperature and humidity sensor 82 which detects the temperature and humidity of the space formed between the mounting section 20 and the cover section 12, a memory 100 which stores various types of information, and a control section 120 which performs various types of control. The fingerprint authentication apparatus 1 includes an image acquisition section 40 which is disposed inside the housing 11, reads a fingerprint of the finger 10 mounted on the mounting section 20, and forms an image of the fingerprint.

The housing 11 may be a rectangular parallelepiped which can be provided with the mounting section 20 and the cover section 12 disposed on its upper surface and can incorporate the image acquisition section 40.

The mounting section 20 is in the form of a hollow plate made of, by way of example only, tempered glass and is disposed on the upper surface of the housing 11. The mounting section 20 incorporates the micro cooling unit 81 (to be described in detail below) at its hollow portion. The mounting section 20 has a photocatalytic layer 22 containing a photocatalyst (e.g., titanium oxide) formed at a surface touched by the finger 10. The micro cooling unit 81 is connected to the control section 120 (to be described in detail below), and its operation is controlled in accordance with instructions from the control section 120.

A positioning section 23 which positions the finger 10 so as to prevent rotation and displacement of the finger 10 when the finger 10 is mounted on the mounting section 20 is disposed around the mounting section 20 on the upper surface of the housing 11. The positioning section 23 includes a finger tip contact section 23A which is located closer to the front side of a finger insertion direction than the mounting section 20 and with which a tip of the finger 10 comes into contact when the finger 10 is mounted on the mounting section 20, guide sections 23B and 23C which are located on two sides of the mounting section 20 in a direction perpendicular to the finger insertion direction and guide side portions of the finger 10, and a finger root support section 23D which is located opposite to the finger tip contact section 23A and supports a portion near a root of the finger 10.

The image acquisition section 40 is configured to read a fingerprint of a user and form an image of the fingerprint. The image acquisition section 40 includes a light source 41, a prism 42 which is disposed on a lower surface of the mounting section 20, a lens 43 on which light reflected by the prism 42 is incident, and an image sensor 44 on which the light condensed by the lens 43 is incident and which converts the incident light into current signals. The operation of the light source 41 and the image sensor 44 is controlled in accordance with instructions from the control section 120 (to be described in detail below).

The cover section 12 is disposed on the upper surface of the housing 11. The cover section 12 has a finger port 14 into/from which the finger 10 of the user is to be inserted/removed, and a front end in the finger insertion direction of the cover section 12 is closed. The cover section 12 is dome-shaped to cover the mounting section 20 and the positioning section 23.

The finger sensor 61 is disposed in a region of an inner surface 13 of the cover section 12 where the finger sensor 61 can detect whether a finger is mounted on the mounting section 20. More specifically, as shown in FIG. 4, the finger sensor 61 is disposed in a region facing a region between the mounting section 20 and the finger tip contact section 23A. The finger sensor 61 is connected to a finger detection section 121 which is a component of the control section 120 (to be described in detail below).

Note that an existing human body sensor such as an infrared ray sensor can be used as the finger sensor 61. For example, an ultraviolet light-emitting diode, an LED black light, or the like can be used as each ultraviolet irradiation lamp 62A, 62B, or 62C. An existing LED black light, for example as introduced in "Keitaigata shigaisen (365/370/375 nm) LED 128-to ogata ratio" (handheld light of a large size with 128 ultraviolet (365/370/375 nm) LEDs), OPTOCODE CORPORATION, can be used as the LED black light.

The ultraviolet irradiation lamps 62A, 62B, and 62C are spaced adjacent to one another in parallel to the insertion direction of the finger 10 in a region facing the mounting section 20 of the inner surface 13 of the cover section 12. These ultraviolet irradiation lamps 62A, 62B, and 62C are connected to an ultraviolet irradiation control section 122 which is a component of the control section 120 (to be described in detail below).

The micro cooling unit 81 is incorporated in the mounting section 20. The micro cooling unit 81 is connected to a cooling section 125 which is a component of the control section 120 (to be described in detail below).

A micro cooling system can be obtained by combining a boiling microchannel which applies a boiling phenomenon with the highest heat removal capacity to circulate fluorine-containing liquid as a refrigerant in the microchannel with a micropump which uses lithographic microfabrication technology, has no movable mechanical part, and is driven at a low voltage can be used as the micro cooling unit 81. The micro cooling unit 81 may be similar to one disclosed in, e.g., "Shosupesu de 100 W/cm2 ijo no reikyakunoryoku wo motsu maikuro kuringu shisutemu wo jitsugen" (Implementation of a micro cooling system with a cooling capacity of 100 W/cm2 or more in a smaller space), Industrial Technology Research Grant Program Press Release Vol. 35, New Energy and Industrial Technology Development Organization and Networking and Computing Service Center, Yamagata University. The foregoing reference is incorporated by reference in its entirety.

The temperature and humidity sensor 82 is disposed on the front end side in the insertion direction of the cover section 12. The temperature and humidity sensor 82 is connected to a temperature and humidity detection section 123 which is a component of the control section 120 (to be described in detail below).

An example of a temperature and humidity sensor is introduced in "Digital humidity and temperature sensor," SysCom, Inc., and can be used as the temperature and humidity sensor 82.

The memory 100 is connected to the control section 120 and stores various types of information such as fingerprint information of the user and information indicating the relationship between the temperature and the humidity and the dew-point temperature.

The control section 120 includes the finger detection section 121, which detects the finger 10 being mounted on the mounting section 20. The control section 120 includes the ultraviolet irradiation control section 122, which controls the ON/OFF states of the ultraviolet irradiation lamps 62A, 62B, and 62C. The control section 120 includes the temperature and humidity detection section 123, which detects temperature and humidity by means of the temperature and humidity sensor 82. The control section 120 includes a dew-point temperature calculation section 124, which calculates dew-point temperature from the temperature and humidity detected by the temperature and humidity detection section 123. The control section 120 includes a cooling section 125, which cools the temperature of the upper surface of the mounting section 20 by means of the micro cooling unit 81. The control section 120 includes a light projection control section 126 which controls the ON/OFF state of the light source 41. The control section 120 includes an image processing section 127, which performs image processing using image signals outputted by the image sensor 44. The control section 120 includes a fingerprint authentication section 128, which compares fingerprint information obtained from the image signals by the image processing section 127 with fingerprint information registered (stored) in advance in the memory 100 and performs authentication. The sections are implemented as functional modules when a CPU in the control section 120 executes a predetermined program stored in the memory 100 or the like. Each section may be constructed using an integrated circuit such as an ASIC.

In some embodiments, an existing configuration used in a conventional fingerprint authentication apparatus may be adopted as a configuration associated with fingerprint authentication in the fingerprint authentication apparatus 1.

Figure 6:
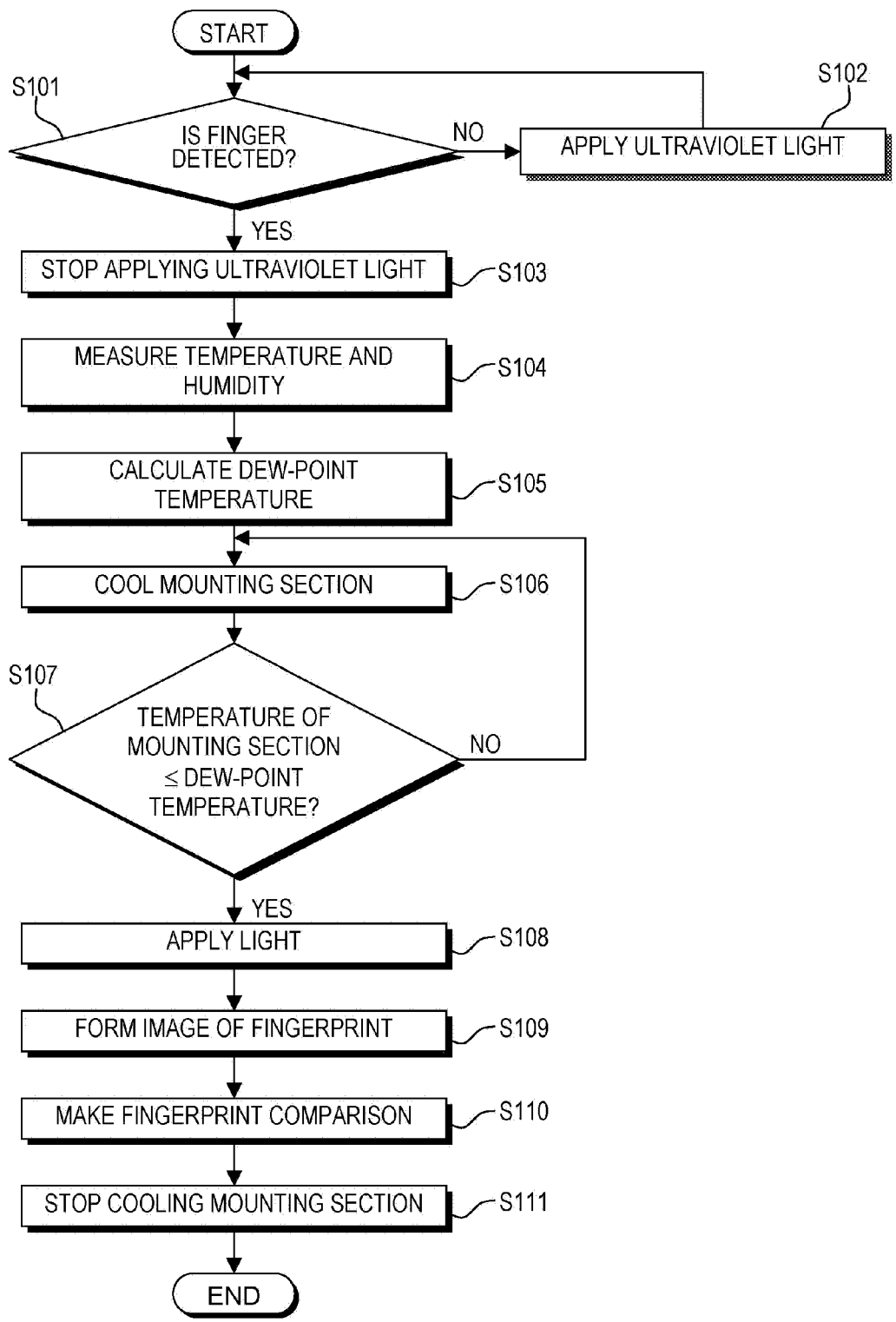
FIG. 6 is a flow chart showing an illustrative example of the operation of the fingerprint authentication apparatus shown in FIG. 1.

The operation of the fingerprint authentication apparatus 1 according to some embodiments will be described with reference to the flow chart shown in FIG. 6, which is a flow chart showing an illustrative example of the operation of the fingerprint authentication apparatus.

First, in step S101, the finger detection section 121 determines whether the finger sensor 61 has detected the finger 10 (i.e., whether the finger 10 has been mounted on the mounting section 20). If the finger 10 has not been detected (NO in step S101), the flow advances to step S102. If the finger 10 has been detected (YES in step S101), the flow advances to step S103.

In step S102, the ultraviolet irradiation control section 122 turns on the ultraviolet irradiation lamps 62A, 62B, and 62C and applies ultraviolet light toward the mounting section 20. Since the photocatalytic layer 22 is formed on the mounting section 20, the ultraviolet light and a photocatalyst react with each other to generate active oxygen. Accordingly, even if viruses or bacteria are present on or near the mounting section 20, the viruses or bacteria can be efficiently killed, which prevents infection from the viruses or bacteria.

In step S103, the ultraviolet irradiation control section 122 turns off the ultraviolet irradiation lamps 62A, 62B, and 62C, and the method advances to step S104. In step S104, the temperature and humidity detection section 123 detects the temperature and humidity in the cover section 12, and the flow advances to step S105. In step S105, the dew-point temperature calculation section 124 calculates dew-point temperature from the temperature and humidity detected by the temperature and humidity detection section 123, and the method advances to step S106.

In step S106, the cooling section 125 starts cooling by means of the micro cooling unit 81 and lowers the temperature of the upper surface of the mounting section 20. After that, the method advances to step S107. In step S107, the cooling section 125 determines whether the upper surface of the mounting section 20 has been cooled to the dew-point temperature calculated by the dew-point temperature calculation section 124 or less. If the upper surface of the mounting section 20 has been cooled to the dew-point temperature or less (YES in step S107), the method advances to step S108. If the temperature of the upper surface of the mounting section 20 is higher than the dew-point temperature (NO in step S107), the method returns to step S106.

Cooling of the upper surface of the mounting section 20 to the dew-point temperature causes slight natural condensation on the upper surface, and adequate moisture can be provided between the finger 10 and the upper surface (the finger-bearing surface) of the mounting section 20. This improves a success rate of fingerprint identification and allows quick and accurate fingerprint authentication. A substance (e.g., molecular sieves or silica gel) which absorbs moisture caused by cooling by means of the micro cooling unit 81 may be disposed inside the mounting section 20.

In step S108, the light projection control section 126 turns on the light source 41, and the flow advances to step S109. When the light source 41 is turned on, light applied from the light source 41 is incident on the prism 42. Since the mounting section 20 is disposed on the prism 42, and the finger 10 is mounted on the mounting section 20, the light incident on the prism 42 is reflected by the finger 10 and a surface of the mounting section 20 in contact with a surface of the prism 42. The light is condensed by the lens 43 and is incident on the image sensor 44. The image sensor 44 converts the incident light into image signals and inputs the image signals to the image processing section 127.

In step S109, the image processing section 127 converts the image signals inputted from the image sensor 44 into fingerprint information, and the method advances to step S110. In step S110, the fingerprint authentication section 128 compares the fingerprint information obtained by the image processing section 127 with fingerprint information registered in advance in the memory 100 and performs authentication. After that, the method advances to step S111, and the cooling section 125 stops cooling by means of the micro cooling unit 81.

A fingerprint authentication apparatus according to embodiments of the present disclosure can be used in various contexts such as personal authentication in an ATM at a financial institution, personal authentication associated with preservation of confidentiality and the like in a company, personal authentication associated with entry and exit and the like, and personal authentication at the time of entering and leaving a building, a room, or the like.

Embodiments include a case where a single control section performs control of a mechanism for authenticating a fingerprint, control of a mechanism for preventing infection from viruses or bacteria, and control of a mechanism for moistening the finger 10 mounted on the mounting section 20. However, embodiments disclosed herein are not limited to this. These types of control may be performed by separate control sections.

This embodiment has described a case where fingerprint authentication is performed using an existing optical sensor as the image acquisition section 40. However, embodiments of the disclosure are not limited to this, and the image acquisition section 40 is not particularly limited. Any other sensor such as a capacitive sensor, a field intensity measuring sensor, or a pressure-sensitive sensor may be used as far as it performs fingerprint authentication by an existing method.

Embodiments include a case where the micro cooling unit 81 and the temperature and humidity sensor 82 are disposed in order to moisten the finger 10 mounted on the mounting section 20. The cooling section 125 and the temperature and humidity detection section 123 for controlling the micro cooling unit 81 and the temperature and humidity sensor 82, respectively, are disposed in the control section 120. However, embodiments of the disclosure are not limited to this. If the fingerprint authentication apparatus is provided with an authentication section which exhibits a high success rate of fingerprint identification even for dry fingers or if the temperature and humidity in a room where the fingerprint authentication apparatus is placed is controlled throughout the year so that the finger 10 of the user is not too dry to affect fingerprint authentication, the micro cooling unit 81, the temperature and humidity sensor 82, the cooling section 125, and the temperature and humidity detection section 123 need not be provided.

Embodiments include a case where the finger sensor 61 and the ultraviolet irradiation lamps 62A, 62B, and 62C are disposed in order to prevent infection from viruses or bacteria. The finger detection section 121 and the ultraviolet irradiation control section 122 for controlling the finger sensor 61 and the ultraviolet irradiation lamps 62A, 62B, and 62C, respectively, are disposed in the control section 120.

In another aspect of some embodiments of the disclosure, the finger sensor 61, the ultraviolet irradiation lamps 62A, 62B, and 62C, the finger detection section 121, and the ultraviolet irradiation control section 122 need not be provided. The fingerprint authentication apparatus may be one with an improved success rate of fingerprint identification which is provided with the micro cooling unit 81, the temperature and humidity sensor 82, the cooling section 125, and the temperature and humidity detection section 123.

Embodiments include a case where the three ultraviolet irradiation lamps 62A, 62B, and 62C are disposed as an ultraviolet irradiation section. However, embodiments of the disclosure are not limited to this. The number of ultraviolet irradiation sections, the intensity of ultraviolet light, and the like may be arbitrarily set as far as the ultraviolet irradiation sections apply ultraviolet light toward the mounting section 20.

Embodiments include a case where the photocatalytic layer 22 is formed on the upper surface of the mounting section 20. However, embodiments of the disclosure are not limited to this. The photocatalytic layer 22 need not be formed.

Embodiments include a case where dew-point temperature is calculated from temperature and humidity measured by the temperature and humidity sensor 82. However, embodiments of the disclosure are not limited to this. For example, an existing dew-point instrument may be disposed, and the dew-point temperature may be measured by the dew-point instrument.

What is claimed is:

1. A fingerprint authentication apparatus, comprising:
a mounting section having a surface configured to receive at least a portion of a finger;
at least one ultraviolet irradiation source adjacent the mounting section; and
a control section, comprising:
a finger detection section configured to detect a presence of the finger received by the mounting section; and
an ultraviolet irradiation control section configured to selectively deactivate the at least one ultraviolet irradiation source when the presence of the finger is detected by the finger detection section.

2. The fingerprint authentication apparatus of claim 1, wherein the ultraviolet irradiation control section is further configured to selectively activate the at least one ultraviolet irradiation source when the finger detection section fails to detect the presence of the finger.

3. The fingerprint authentication apparatus of claim 1, further comprising a cover section disposed over the mounting section and defining a space between the cover section and the mounting section.

4. The fingerprint authentication apparatus of claim 3, wherein the finger detection section is disposed on an inner surface of the cover section facing a region between the mounting section and a finger-tip contact section located at an end of the fingerprint authentication apparatus opposite an insertion end.

5. The fingerprint authentication apparatus of claim 1, further comprising:
a temperature and humidity sensor disposed adjacent the mounting section; and
a dew-point temperature calculation section configured to calculate a dew-point temperature from temperature and humidity detected by the temperature and humidity sensor.

6. The fingerprint authentication apparatus of claim 1, further comprising a photocatalytic material on at least a portion of the surface of the mounting section.

7. The fingerprint authentication apparatus of claim 6, wherein the at least one ultraviolet irradiation source is positioned to apply ultraviolet light to the photocatalytic material.

8. The fingerprint authentication apparatus of claim 1, further comprising a cooling section configured to cool the mounting section.

9. The fingerprint authentication apparatus of claim 1, wherein the at least one ultraviolet irradiation source comprises a plurality of irradiation devices.

10. The fingerprint authentication apparatus of claim 3, wherein the at least one ultraviolet irradiation source is disposed on an inner surface of the cover section overlying the surface of the mounting section.

11. A fingerprint authentication apparatus, comprising:
a mounting section configured to engage with at least a portion of a finger;
an authentication section configured to authenticate a fingerprint of the finger when engaged with the mounting section;
a cover section disposed over the mounting section and defining a space between the mounting section and the cover section, wherein the defined space is effective to receive the at least a portion of the finger;
a temperature and humidity sensor in a region of the cover section overlying the mounting section;
a dew-point temperature calculation section coupled to the sensor and configured to calculate dew-point temperature based on a temperature and a humidity detected by the sensor; and
a cooling section coupled to a cooling unit within a hollow portion of the mounting section and configured to cool a surface of the mounting section to the dew-point temperature.

12. The fingerprint authentication apparatus of claim 11, wherein the dew-point temperature calculation section is configured to calculate the dew-point temperature based on the temperature and the humidity within the space detected by the sensor.

13. The fingerprint authentication apparatus of claim 11, further comprising at least one ultraviolet irradiation source disposed on a surface of the cover section opposing a surface of the mounting section.

14. The fingerprint authentication apparatus of claim 13, wherein a photocatalyst overlies the surface of the mounting section adjacent the at least one ultraviolet irradiation source.

15. The fingerprint authentication apparatus of claim 13, further comprising:
a finger detection section configured to detect a presence of the at least a portion of the finger engaged with the mounting section; and
an ultraviolet irradiation control section configured to selectively activate the at least one ultraviolet irradiation source when the finger detection section detects an absence of the finger engaged with the mounting section.

16. A method for authenticating a fingerprint, comprising:
measuring a temperature and a humidity within a space formed between a mounting section and a cover section, the space configured to receive at least a portion of a finger;
calculating a dew-point temperature from the temperature and the humidity measured within the space;
cooling at least a portion of a surface of the mounting section configured to receive the finger to a temperature of less than or equal to the dew-point temperature; and
authenticating a fingerprint of the finger with the mounting section cooled to the dew-point temperature.

17. The method of claim 16, wherein cooling at least the portion of the surface of the mounting section comprises forming condensation on the surface of the mounting section to moisten at least a portion of the finger.

18. The method of claim 16, further comprising:
detecting a presence of the finger engaged with a surface of the mounting section; and
activating an ultraviolet irradiation source effective to apply ultraviolet light to the surface of the mounting section when the presence of the finger is not detected.

19. The method of claim 16, further comprising:
determining whether an upper surface of the mounting section has been cooled to a temperature of less than or equal to the dew-point temperature using a temperature and humidity sensor; and
when the mounting section is cooled to a temperature of less than or equal to the dew-point temperature, activating a light source such that light applied from the light source is incident on a prism on which the mounting section is disposed.

* * * * *

UNITED STATES PATENT AND TRADEMARK OFFICE
CERTIFICATE OF CORRECTION

PATENT NO. : 8,487,988 B2  
APPLICATION NO. : 13/362062  
DATED : July 16, 2013  
INVENTOR(S) : Oguchi Page 1 of 1

It is certified that error appears in the above-identified patent and that said Letters Patent is hereby corrected as shown below:

On the Title Page, in Item (56), under "OTHER PUBLICATIONS", in Column 2, Line 1, delete "al "Effects of batericidal" and insert -- al., "Effects of bactericidal --, therefor.

On Title Page 2, in Item (56), under "OTHER PUBLICATIONS", in Column 2, Line 6, delete "100w/Cm 2" and insert -- 100w/Cm2 --, therefor.

Signed and Sealed this  
Twenty-ninth Day of October, 2013

Teresa Stanek Rea  
*Deputy Director of the United States Patent and Trademark Office*